United States Patent
Aoyagi et al.

(10) Patent No.: US 6,299,867 B1
(45) Date of Patent: Oct. 9, 2001

(54) ADSORBENT

(75) Inventors: Juuro Aoyagi, Tokyo; Ryuichi Endo, Chiba, both of (JP)

(73) Assignee: Kouki Bussan Yugenkaisha (JP)

(*) Notice: Subject to any disclaimer, the term of this patent is extended or adjusted under 35 U.S.C. 154(b) by 0 days.

(21) Appl. No.: 09/230,387

(22) PCT Filed: Dec. 27, 1996

(86) PCT No.: PCT/JP96/03891
  § 371 Date: Jan. 22, 1999
  § 102(e) Date: Jan. 22, 1999

(87) PCT Pub. No.: WO98/03259
  PCT Pub. Date: Jan. 29, 1998

(51) Int. Cl.$^7$ ............... A61L 9/00; A61L 9/015; A61L 9/04
(52) U.S. Cl. .......... 424/76.1; 424/76.2; 424/76.3; 424/76.5; 424/77
(58) Field of Search ............... 424/76.1, 76.2, 424/76.3, 76.5, 77, 78.08

(56) References Cited

U.S. PATENT DOCUMENTS 5,510,166 * 4/1996 Inoue et al. ............... 428/76

FOREIGN PATENT DOCUMENTS

| 55-42210 | 3/1980 | (JP). |
|---|---|---|
| 55-95611 | 7/1980 | (JP). |
| 62-207220 | 9/1987 | (JP). |
| 62-207220 A | * 11/1987 | (JP). |
| 3-204803 | 9/1991 | (JP). |
| 06157807 | 6/1994 | (JP). |
| 63-71158 | 3/1998 | (JP). |
| 93/12877 | 7/1993 | (WO). |

* cited by examiner

Primary Examiner—Thurman K. Page
Assistant Examiner—S. Tran
(74) Attorney, Agent, or Firm—Mathews, Collins, Shepherd & Gould, P.A.

(57) ABSTRACT

An adsorbent is disclosed which is formed either by coating an adsorption mass such as active carbon with a gel-like substance such as the dibasic metallic salt of a macromolecular polycarboxylic acid, soybean curd, jelly, konjak, agar, perilla, gelidium jelly, or chitosanoxalic acid salt gel and subsequently subjecting the coated basis to a freezing treatment or by effecting the coating with the gel-like substance already made to contain a frost damage preventing substance such as glycerin and subsequently depriving the coated basis of the frost damage preventing substance. This adsorbent, on being brought into direct contact with foodstuffs or ingested directly into the digestive system, effects highly efficient removal by adsorption of such food additive, feed additive, agricultural pesticide, food poisoning substance, allergen, heavy metal or highly poisonous organic compound as are suffered to adhere to or exist in the foodstuffs, such surplus nutrients as persist in the digestive system, such oligomers and additives as are contained in liquors, such metabolites of alcohol as are formed in the digestive system after assimilation of alcohol, such harmful substances as hydroperoxides of unsaturated fatty acids as are suffered to exist in oils and fats, and such components of offensive odor as emanate from fish.

18 Claims, No Drawings

ADSORBENT

TECHNICAL FIELD

This invention relates to a novel adsorbent to be used in agents for the removal of harmful substances by adsorption. More particularly, the invention relates to an adsorbent which is formed by coating an adsorption basis with a gel-like substance.

BACKGROUND ART

The active carbon possesses a large specific surface area and exhibits a great ability to effect adsorption and finds utility as a representative adsorbent in various applications. When the active carbon is directly ingested into the digestive system as a medicinal carbon for the purpose of removing by adsorption such substances as induce autointoxication, medicinal poisoning, etc. however, it is liable to do harm by causing constipation. When an effort is made to mingle the active carbon with a foodstuff and ingest the mixture into the digestive system, it is at a disadvantage in imparting an unpleasant sensation to the palate and smearing the foodstuff in a blackish tint. It is also known that in the animal cell, the active carbon in a finely divided state is adsorbed on the protein or sugar protein in the outer layer of the cell membrane. When the active carbon in the finely divided state is directly ingested into the digestive system as an agent for the removal of a harmful substance by adsorption, it is suspected that part thereof persists in a state adsorbed on the cells in the digestive system with fastness such that thorough elimination thereof from the digestive system may be extremely difficult.

With a view to solving this problem, adsorbents formed by coating active carbon with water-insoluble mannan such as konjak or with a cross-linked polymer such as calcium alginate have been proposed (JP-A-55-95,611 and JP-A-04-210,239). Since these adsorbents result from forming a surface coat on the particles of active carbon, they suffer from such problems as inducing a decrease in the surface area and impeding ample manifestation of the ability of adsorption inherent in the active carbon.

This invention has been created in the light of the problem encountered by the prior art as described above. It has for an object thereof the provision of an adsorbent which keeps intact the ability of adsorption inherent in the adsorption basis such as of active carbon and, on being brought into direct contact with foodstuffs or ingested directly into the digestive system, effects highly efficiently the removal by adsorption of such harmful substances as are suffered to adhere to or mingle into the foodstuffs or suffered to occur in the digestive system.

DISCLOSURE OF THE INVENTION

The object mentioned above is accomplished by this invention providing an adsorbent which is formed by coating an adsorption basis with a gel-like substance and subsequently subjecting the coated basis to a freezing treatment.

The object is further accomplished by this invention providing an adsorbent which is formed by coating an adsorption basis with a gel-like substance already containing a frost damage preventing substance and subsequently depriving the coated basis partly or wholly of the frost damage preventing substance.

This invention further concerns the adsorbent, wherein the frost damage preventing substance mentioned above is glycerin.

This invention further concerns the adsorbent, wherein the adsorption basis mentioned above is a carbonaceous material possessing the ability to effect adsorption.

This invention further concerns the adsorbent, wherein the carbonaceous material possessing the ability to effect adsorption is active carbon or charcoal.

This invention further concerns the adsorbent, wherein the gel-like substance mentioned above is the divalent metallic salt of a macromolecular polycarboxylic acid.

This invention further concerns the adsorbent, wherein the divalent metallic salt of the macromolecular polycarboxylic acid mentioned above is calcium alginate.

This invention further concerns the adsorbent, wherein the gel-like substance mentioned above is soybean curd, jelly, konjak, agar, perilla, gelidium jelly, or chitosanoxalic acid salt gel.

This invention further concerns the adsorbent which is formed by drying the adsorbent mentioned above.

This invention further concerns the adsorbent which comprises an adsorbent moiety formed by coating an adsorption basis with a first gel-like substance and a second gel-like substance moiety.

This invention further concerns the adsorbent which is formed by seasoning either the adsorbent moiety mentioned above or the second gel-like substance moiety mentioned above.

This invention further concerns the adsorbent wherein the adsorbent moiety mentioned above comprises any of the adsorbents mentioned above.

This invention further concerns an agent for the removal by adsorption of a harmful substance, which agent comprises any of the adsorbents mentioned above.

This invention further concerns an agent for removal by adsorption of a harmful substance, wherein the harmful substance mentioned above is a food additive, a feed additive, an agricultural pesticide, a food poisoning substance, allergen, a heavy metal, or a strongly poisonous organic compound which is suffered to adhere to or mingle in a foodstuff or an animal feed or assimilated into the digestive system.

This invention further concerns the agent mentioned above for removal by adsorption of a harmful substance, wherein the feed additive mentioned above is an antibiotic substance, a synthetic antibacterial agent, or a hormone.

This invention further concerns the agent mentioned above for removal by adsorption of the harmful substance, wherein the food poisoning substance mentioned above is exotoxins, autotoxins, or a harmful chemical substance.

This invention further concerns the agent for removal by adsorption of a harmful substance, wherein the agent mentioned above is formed of the adsorbent mentioned above and the harmful substance mentioned above is formed of an antibiotic substance which has either undergone oral ingestion or acted on the intestinal bacteria.

This invention further concerns the agent for removal by adsorption of a surplus nutrient assimilated in the digestive system, wherein the agent mentioned above is formed of the adsorbent mentioned above.

This invention further concerns the agent for removal by adsorption of the metabolite of alcohol formed in the digestive system in consequence of the assimilation of the alcohol, wherein the agent mentioned above is formed of the adsorbent mentioned above.

This invention further concerns the agent for removal by adsorption of the hydroperoxide of an unsaturated fatty acid, wherein the agent mentioned above is the adsorbent mentioned above.

This invention further concerns a deodorant formed of the adsorbent mentioned above.

This invention further concerns a processed foodstuff or animal feed incorporating therein the adsorbent mentioned above in an amount in the range of 0.01–6 wt. %.

This invention further concerns the processed foodstuff mentioned above which is a dairy product, a product of fish paste, a processed fish or shellfish, a processed meat, processed beans, processed vegetables, a processed potato, a processed cereal, a sweetener, oil and fat, or a cake.

It is considered that when the adsorbent of this invention is formed by coating an adsorption basis with a gel-like substance and then subjecting the coated basis to a freezing treatment, this adsorbent is enabled to keep intact the ability to effect adsorption possessed inherently by the adsorption basis because the moisture in the gel-like substance forming the coat is coagulated and is consequently allowed to form in the coat such minute pores as have a larger diameter than the pores which would be formed solely by cross-linkage.

It is considered that when the adsorbent is formed by coating the adsorption basis with the gel-like substance already containing a frost preventing substance and then depriving the coated basis of the frost preventing substance, this adsorbent is enabled to manifest the same effect as mentioned above because the procedure so employed produces similar minute pores in the gel-like substance forming the coat.

When the adsorbent of this invention uses minute particles of powdered active carbon, for example, as the adsorption basis, it assumes the constitution of a dispersion system having the adsorption basis uniformed dispersed in the gel-like substance. The adsorbent, therefore, permits highly efficient removal by adsorption of a harmful substance because the adsorbent in its entirety enjoys an increase in the surface area available for adsorption and a consequent increase in the ability to effect adsorption as compared with the adsorbent produced by solely using active carbon in a highly dispersed state.

Since the adsorbent of this invention has the adsorption basis coated with the gel-like substance, it can be directly ingested into the digestive system and utilized therein for effecting ready removal by adsorption of a harmful substance which has mingled in a foodstuff and consequently succumbed to assimilation therein. The adsorbent, on being directly ingested into the digestive system, does not induce such adverse effects as constipation. The adsorbent which has effected the removal by adsorption of the harmful substance in the digestive system can be very quickly and easily discharged from the digestive system.

The adsorbent of this invention is only required to mingle into or contact a foodstuff to implement the removal by adsorption of the harmful substance contained in the foodstuff. In this case, the adsorbent which has effected the removal of the harmful substance by adsorption can be separated easily and quickly from the foodstuff as compared with the adsorbent which is used all by itself. Further, even when the adsorbent escapes the separation and entrains the foodstuff and succumbs to assimilation in the digestive system, it warrants safety because it can be quickly discharged from the digestive system as mentioned above.

The adsorbent of this invention can be utilized by being mixed with a processed foodstuff besides being directly ingested into the digestive system as described above. When the adsorbent of this invention is mixed with the processed foodstuff and the resultant mixture is put to use for eating, it produces no sensation of the presence of foreign particles, excels in palatability, and avoids polluting the food material in a black tint.

The adsorbent of this invention can be utilized for animals being raised besides being utilized for human beings as an agent for the removal by adsorption of substances harmful to human beings. The adsorbent of this invention can be utilized for treating animal feed or it can be utilized for directly feeding the animals or by being mixed with the animal feed prepared for feeding the animals.

BEST MODE FOR CARRYING OUT THE INVENTION

The adsorbent of this invention can be obtained by coating an adsorption basis with a gel-like substance and subsequently subjecting the coated basis to a freezing treatment.

As concrete examples of the adsorption basis to be used in the production of the adsorbent of this invention, active carbon, charcoal, alumina, silica gel, zeolite, bentonite, calcium phosphate, ion-exchange resin, and chelating resin may be cited. Among other adsorption bases mentioned above, such carbonaceous materials as active carbon and charcoal which possess the ability to effect adsorption prove favorable. The active carbon proves particularly suitable.

When the active carbon is used as the adsorbent, it can be used in various forms such as, for example, powder, granules, and fibers. It is nevertheless particularly favorable to use the active carbon in the powdery or granular form. In this case, the active carbon is preferred to have a particle diameter in the range of 5 $\mu$–10 mm. If the particle diameter of the active carbon is less than 5 $\mu$m, the active carbon will not be handled easily. If the particle diameter exceeds 10 mm, the ability of the active carbon to effect adsorption per unit weight will be unduly low. The amount of the active carbon to be incorporated in the gel-like substance is preferred to be in the range of 0.02–90 wt. %. If this amount of the active carbon is less than 0.02 wt. %, the active carbon will not be sufficiently effective in attaining necessary adsorption. If the amount exceeds 90 wt. %, the active carbon will be dispersed in the gel-like substance only with difficulty.

As the gel-like substance to be used in the adsorbent of this invention, the gel-like substance such as, for example, the divalent metal salt of a macromolecular polycarboxylic acid which, when injected into the digestive system, does no harm may be cited. As concrete examples of the divalent metal salt of a macromolecular polycarboxylic acid, calcium, magnesium, iron, and copper salts of such macromolecular compounds as alginic acid, pectic acid, carboxymethyl cellulose, carboxymethyl chitin, styrene-maleic acid copper, styrene-maleic acid semialkyl ester copolymer, ethylene-acrylic acid copolymer, polyacrylic acid, polymethacrylic acid, acrylic acid-methacrylic acid copolymer, acrylic acid-maleic acid copolymer, and acrylic acid-maleic acid semialkyl ester copolymer which possess a carboxyl group in the side chain may be cited.

The adsorbent which uses the divalent metal salt of a macromolecular polycarboxylic acid is obtained by adding the suspension of an alkali metal salt or an ammonium salt of a macromolecular polycarboxylic acid and an adsorption basis such as, for example, active carbon powder dropwise into an aqueous divalent metal salt solution. The concentration of the alkali metal salt or ammonium salt of the macromolecular polycarboxylic acid in the suspension mentioned above is preferred to be in the range of 0.01–5 mols. If the concentration is less than the lower limit of the range, the gel thoroughly coating or dispersing the adsorption basis will not be obtained. If the concentration exceeds the upper limit, the amount of the salt of the macromolecular carboxylic acid which surrounds the adsorption basis will be so large as to impede the infiltration of a substance for adsorption into the adsorption basis and degrade conspicuously the ability of the adsorbent to effect necessary adsorption. The concentration of the aqueous divalent metal salt is preferred to be in the range of 0.05–5 mols. If this concentration is less than the lower limit, the adsorption basis will have no sufficient strength because the ratio of cross-linkage is unduly small. If it exceeds the upper limit, the infiltration of the substance for adsorption into the adsorption basis will be attained with difficulty because the ratio of cross-linkage is unduly large and the pores in the adsorption basis have an extremely small diameter.

The gel-like substances which can be used in this invention include such gel-like foodstuffs as soybean curd, jelly, konjak, agar, perilla, and gelidium jelly and chitosanoxalic acid salt gel, for example. The adsorbent which uses such a gel-like substance is obtained by suitably adding and dispersing the adsorption basis such as, for example, active carbon powder prior to the formation of gel during the course of production of the relevant gel-like foodstuff.

The adsorbent of this invention allows the gel-like substances mentioned above to be used either singly or in the form of a mixture of two or more members. This adsorbent, as occasion demands, allows addition thereto of such viscosity enhancers as almond gum, AEROMONASU gum, ASOTOBAKUTAA, BINERANJII gum, AMASHIIDO gum, gum arabic, arabinogalactan, alginic acid, AROEBERA extract, UERAN gum, ERUWINIA, MITSUENSHISU gum, EREMI resin, ENTEROBAKUTAA.MITSUENSHISU gum, ENTEROBAKUTAA gum, ORAKU extract, KAADORAN, seaweed cellulose, KASHIA gum, brown seaweed extract, KARAGINAN, karaya gum, KAROBUBIIN gum, GACHII gum, xanthan gum, KITACHIAROE extract, chitin, chitosan, guayule gum, glucosamine, yeast cell membrane, SAIRYUMUSHIIDO gum, JURAN gum, SUKURERO gum, YASURERO gum, SESUBANIA gum, TAMARINDOSHIIDO gum, TARA gum, DANMARU resin, PUKISUTOSSO, tragacanth gum, TORIAKANSOSU gum,TOROROAOI, Bacillus natto gum, fibrinous cellulose, NOASERERAN, ZORURAN, pectin, MAKUROHOMOBUSHISU gum, RAMUZAN gum, and levan, such gum bases as ERENU resin, OURIKYURIROU, OZOKERAITO, NABOBANAKKUSU resin, KAURI gum, carnauba wax, KANDERIWO wax, whale wax, crown gum, gutta KACHU, gutta HANKAN, gutta BERUKA, guaiac resin, guayule, KOOPARU resin, KOPAIPAPARUSAMU, rice bran wax, rum, decomposed rubber resin, sugar cane wax, SANDARAKKU resin, Shellac (refined shellc and white shellac), shellc wax, JURUTON, SORUBA, SORUBINBA, talc, DAMMARU resin, CHIKUBURU, chicle, TSUMEE, low molecular rubber, NYUKOU, nigger gutta, NITSUBERO, balata, paraffin socks, fur balsam, powdered pulp, powdered rice hull, Venezuela chicle, benzoin gum, BERIIJO, HOHOBA wax, MASSARANDOBA chocolate, MASSARANDO BABARATA, microcrystalline socks, mastic, honey wax, myrrh, sumac wax, montan wax, oilcake seed wax, lanolin, RETCHUBUBAKA, ROJIKINHA, and rosin, such brighteners as OURIKYURI wax, carnauba wax, KANDERIRA wax, whale wax, coriander seed, saffron, prickly ash, perilla, SYAROTTO, JUNIBAA berry, ginger, cinnamon, star anise oil, spearmint, sage, SEBORII, celery seed, thyme, water pepper, onion, tarragon, chicory, CHAIBU, CHAABIRU, extracted powder spice, Chile pepper, dill, nutmeg, leek, garlic, scallion, parsley, peppermint, paprika, pistachio, FENUGU leek, FENNERU seed, horse raddish, MAAJORAN, umbrelliferous plant, Japanese ginger, mace, MESU, citron, lime, red pepper, lemon, rosemary, laurel, and horse raddish, such dairy products as cheese, fresh cream, butter, powdered milk, whey, and condensed milk, such liquors as curano, Kirschwasser, sherry, refined sake, beer, wine, brandy, powdered sake, vermouth, rum, and liqueur, and alpha starch, alpha rice, sweetened bean paste, UURON tea, EROUTEROKOKKU extract, dried vegetable, agar, gluten, chlorella, powdered blood, powdered blood plasma, koji mold, black tea, coffee, yeast, ginseng, cocoa, powdered rice, corn flour, wheat malt, collagen, powdered konjak, acetobacter, sake lees, jam, table salt, protein from refined fish meat, protein from refined flour, protein from refined soybean, gelatin, buckwheat flour, seed malt, chocolate, dextrin, starch, corn flour, Bacillus subtilis, sparingly digestible dextrin, lactobacillus, lactose, malt, malt extract, ham, bifidobacterium bifidum, bran, partially alpha starch, powdered potato, powdered yam, monascus, hemicellulose, ground tea, citrous pulp, powdered egg yolk, egg yolk oil, albumen, and green tea.

The adsorbent of this invention can be otherwise obtained by coating an adsorption basis with a gel-like substance already containing a frost harm preventing substance and subsequently depriving the coated basis partly or wholly of the frost harm preventing substance.

As concrete examples of the frost harm preventing substance to be used in the adsorbent of this invention, acetamide, L-alanine, albumin, ammonium acetate, chloroform, choline, dextran, diethylene glycol, dimethyl acetamide, dimethyl formamide, dimethyl sulfone, dimethyl sulfoxide, erythritol, ethanol, ethylene glycol, formamide, glucose, glycerin, glycine, hydroxy ethyl starch, inositol, lactose, magnesium chloride, magnesium phosphate, maltose, mannitol, mannose, methanol, methyl acetamide, methyl formamide, methyl urea, monoacetin, phenol, polyethylene glycol, polyethylene oxide, polyoxyethylene, polyvinyl pyrrolidone, L-proline, propionamide, propylene glycol, pyridine, N-oxide, resorcinol, ribitol, ribose, L-serine, sodium bromide, sodium chloride, sodium iodide, sodium nitrate, sodium nitrite, sodium sulfate, sorbitol, sucrose, polyethylene glycol, urea, L-valene, and xylose may be cited. Among other frost harm preventing substances cited above, glycerin proves particularly advantageous.

Incidentally, when the adsorbent of this invention is utilized in a form proper for ingestion into the digestive system, the adsorbent itself may be properly seasoned for the purpose of facilitating the ingestion.

The adsorbent of this invention can be used for the purpose of removing by adsorption such harmful substances as food additives, feed additives, agricultural pesticides, food poisoning substances, allergen, heavy metals, and strongly poisonous organic compounds which have been attached to or contained in food or feed or assimilated into the digestive system.

Specifically, the adsorbent of this invention is usable for the removal by adsorption of food additives represented by such sweeteners as saccharin and salts thereof, dipotassium tripotassium glycyrrhizinate, and ethyl acetacetate, such coloring agents as iron sesquioxide, food dye red Nos. 3, 40, 102, 104, 105, and 106, food dye yellow Nos. 4 and 5, food dye green No. 3, food dye blue Nos. 1 and 2, and titanium dioxide, such preserving agents as benzoic acid, orthophenyl phenol, sorbic acid, dehydroacetic acid, propionic acid and salts thereof, diphenyl, thiapentazole, and paraoxybenzoic esters, such quality preserving agents as propylene glycol, such viscosity enhancer-gelling agent.pasting agent as propylene glycol alginate, potassium carboxymethyl cellulose, sodium carboxymethyl cellulose, sodium starch glycolate, sodium starch phosphate, methyl cellulose, and polysodium acrylate, such antioxidants as dl-α-tocopherol, sorbic acid and sodium salt thereof, guaiac resin, isopropyl citrate, dibuyl hydroxy toluene, nordihydro-guaiaretic acid, butylhydroxy anisole, propyl gallate, calcium disodium ethylene-diamine tetraacetate, and disodium ethylene-diamine tetraacetate, such color formers as sodium nitride, potassium nitrate, sodium nitrate, ferric sulfate, and phosphates, such fungicidal agents as hydrogen peroxide, hypochlorous acid, and sodium hypochlorite, such bleaching agents as sulfurous acid and salts thereof, and such antifungous and antibacterial agents as diphenyl and thiapentazole.

As respect agricultural pesticides, the adsorbent of this invention can be applied to the removal by adsorption of fungicides, insecticides, and herbicides using such organic phosphorus compounds as MEP, Diazinone, PAP, IBP, EDDP, DDVP, DEP, Marathione, and EPN, such organic chlorine compounds as Chlorosalonyl, Chloropycrin, D—D, Pyrazolate, PCNB, Flacide, DCIP, and Procimidone, such carbamates as BPMC, MTMC, XMC, MCC, and MIPC, such organic bromine compounds as methyl bromide, such benzoimidazoles as Thiophanate Methyl, such thiocarbamates as Penthiocurb, such diphenyl ethers as CNP, such chlorine compounds as chlorates, such phthalimides as Captan, such dithiocarbamates as Maneb, such bipyridiums as Paracoat, such diphenyl ethers as Chloromethoxynyl, such acid amides as DCPA, such copper compounds as inorganic copper compounds, and such compounds as Sethoxydim, Isoprothioran, Propenazol, Dimuron, and Naproanilide. The other harmful substances that permit effective use of the adsorbent of this invention for the removal by adsorption include such allergens as histamine which causes allergy-like food poisoning and arises from the putrefaction of meat, for example, such heavy metals as mercury, lead, hexavalent chromium, cadmium, selenium, arsenic, copper, iron, and zinc, and such strongly poisonous organic compounds as phosphides, chlorides, and benzene.

The adsorbent of this invention can be also utilized for the removal by adsorption of exotoxins, autotoxins, and harmful chemical substances which are food poisoning substances. As concrete examples of the exotoxins, toxins produced by intestine infecting bacteria such as botulinum-producing toxins (types A–F), clostridium difficile-producing enterotoxin and cytotoxin, clostidium perfringens-producing enterotoxin, toxin protoza escherichia coli-producing readily heatable enterotoxin and thermoduric enterotoxin, dysentery-producing Shiga toxin, staphylococcus-producing enterpotoxins (types A–E), Vibrio cholera-producing cholera toxin, vibrio parahaemolyticus-producing thermoduric hemolytic toxin and enterotoxin, and ersinia entrochocolitica-producing enterotoxin, berotoxins produced by intestine hemorrhagic *E. coli* such as berotoxin, andceleus-producing toxin may be cited. As concrete examples of the autotoxins, tetrodotoxin (toxin of tetraodontiformes), such mushroom toxins as amatoxins, phallotoxins, muscarine, muscaridine, ibotenic acid, bufotenine, muscimol, psilocybin, psilocin, serotinin, gyromitrin (helvellic acid), and illudin, such paralytic shell toxins as succitoxin, neosuccinitoxin, and goniotoxin, such diarrheal shell toxins as dinophicis toxin-1, -3, and pectenotoxin, such toxins of fish and shellfish as vitamin A (poisoning of striped jewfish), penelpin (poisoning of little neck clam), tetramine (poisoning of tetramine), neo-Suruga toxin and pro-Suruga toxin (poisoning of ivory shell), and Pipheoholbyte a (sunlight dermatitis), solanin (potato), atropine, scopolamine, L-hyoscyamine, aconitine, hydrogen cyanide (which exists in the form of a non-toxic hydrocyanic acid complex in the seeds of Japanese apricot, peach, apricot, apple, and pear and gives rise to hydrocyanic acid in the system), 4'-methoxy pyridoxin (poisoning of ginko), and aflatoxin (poisoning of mildew) may be cited. As concrete examples of the harmful chemical substance, methanol, arsenic, cyan compounds, sodium glutamate, sodium saccharine, tin, copper, zinc, cadmium, arsenic compounds, and sodium fluoride may be cited.

Further, by the adsorbent of this invention, such harmful substances as are formed by antibiotic substances which have been orally injected or by antibiotic substances which have acted on the enterobacteria can be removed.

In recent years, the practice of adding antibiotic substances and synthetic antibacterial agents to the feed with a view to promoting the growth of domestic animals, treating the infectious diseases affecting the animals, or preventing the animals from the diseases and the practice of giving hormones such as estrigen to bulls with a view to improving the quality of meat have been in vogue. The manifestation of allergic symptoms and abnormal sexual growths and the development of carcinogenicity of synthetic antibacterial agents due to the consumption of such diary products and meats as contain the ingested additives as residues have come to pose a problem. The adsorbent of this invention can be further utilized for the removal by adsorption of such antibiotic substances as penicillin which persist in diary products and meat, such synthetic antibacterial agents as sulfa drugs, and such feed additives as hormones like progestron and estradiol.

The adsorbent of this invention can be used further for the removal by adsorption of such surplus nutrients as have escaped assimilation in the digestive system. The adsorbent of this invention, in a test for the culture of cells, functions to inhibit the propagation of cells by adsorbing the sources of nutritions in the culture medium. When it is ingested together with hood before or after the meal, it represses the metabolism of the food, for example. It, therefore, can be utilized as an agent for resisting corpulence or for the purpose of dietary cure. Specifically, by substituting the adsorbent of this invention for about 20% of the standard diet, the amount of the nutriment to be adsorbed is substantially lowered to 60–64% because the adsorbent of this invention further removes by adsorption 20–25% of the nutriment of the food. By repeating this substitution while paying attention to the loss of body weight, it is made possible to accomplish the gradual loss of body weight and the ultimate correction of body weight to a proper level. Moreover, this dietary cure can be continued for a long time because the person practicing the dietary cure does not feel hungry or stressful because the amount of the food to be consumed does not change from the standard level.

Further, the adsorbent of this invention can be used for removing by adsorption oligomers and additive substances which are contained in liquors and removing by adsorption acetaldehyde and other metabolites of alcohol which are formed in the digestive system in consequence of the consumption of liquors. Specifically, the metabolism of alcohol (ethyl alcohol) in a mammal gradually advances and forms acetaldehyde as an intermediate metabolite, with the result that the acetaldehyde will be subsequently oxidized into acetic acid and acetyl-CoA. In this metabolism of alcohol, the rise of the concentration of acetaldehyde ultimately induces such symptoms as retch, nausea, facial flush, rise of pulsation, headache accompanied by sudden pulsation, rise of cutaneous temperature, and fall of minimum blood pressure (acetaldehyde symptoms, i.e. so-called hangover). The oligomers and additives which are contained in liquors are also held responsible partly for the symptoms. By taking the adsorbent of this invention during, before, or after the course of drinking thereby removing by adsorption the oligomers and additives contained in the liquors and consequently removing by adsorption the acetaldehyde formed in the digestive system, therefore, it is made possible to preclude or cure such acetaldehyde symptoms. The symptom of poisoning due to erroneous consumption of methanol is similarly caused by the intermediate metabolite of alcohol. The adsorbent of this invention can be utilized likewise for the cure of acidosis.

The adsorbent of this invention can be also used for the removal by adsorption of functional oligomers having molecular weights of 100—some tens of thousand such as, for example, such pathogenic proteins as prion, fatty acids, saccharides, and compounds combining them.

Further, the adsorbent of this invention can be used on persons complaining of medicinal poisoning caused by barbituric acid type drugs, agricultural pesticides, hypnotic drugs, sedative drugs, antidepression drugs, analgesic drugs, drugs for affecting cardiac blood vessels, antibiotic substances, anticancer drugs, and stimulants with a view to effecting removal by adsorption of the relevant medicines.

The adsorbent of this invention can be used for the removal by adsorption of hydroperoxides of unsaturated fatty acids which are responsible for the acid putrefaction of oils and fats such as, for example, edible oils. The acid putrefaction of oils and fats such as, for example, edible oils is chiefly caused by the fact that the unsaturated fatty acids in the oils and fats are autoxidated by the oxygen in the air and consequently caused to form hydroperoxides. The hydroperoxides are further decomposed to produce aldehydes, ketones, and lower fatty acids which have adverse effects on smell and taste. The adsorbent of this invention can be utilized also as an agent for preventing oils and fats from acid putrefaction because it is capable of adsorbing such hydroperoxides of unsaturated fatty acids formed in oils and fats by the autoxidation.

Further, the adsorbent of this invention can be used for the removal by adsorption of offensive odors from fish. To be specific, the adsorbent of this invention can be utilized as a deodorant because it removes by adsorption such volatile salts as ammonia and trimethylamine which are odorous components of fish, such volatile acids as dilute acids and acetic acid, such volatile carbonyl compounds as formaldehyde and acetaldehyde, such volatile sulfur-containing compounds as hydrogen sulfide and methyl mercaptan, such non-carboxyl neutral compounds as alcohols and phenols, and other typical odorous components.

Another aspect of this invention resides in providing a processed food or feed which incorporates the adsorbent therein in anamount in the range of 0.01–60 wt. %. The amount of the adsorbent of this invention incorporated in the processed food, etc. is defined in the range of 0.01–60 wt. % because the processed food will not acquire a sufficient ability to effect necessary adsorption if the amount is less than 0.01 wt. % and the processed food will fail to acquire necessary texture and palatability for food and will suffer from serious sensation of the presence of foreign matter if the amount exceeds 60 wt. %.

As concrete examples of the processed food which permits incorporation of the adsorbent, such dairy products as yogurt and cheese, such pastes of fish meat as kamaboko, chikuwa, hampen, satsumaage, naruto, and tsumire, such processed meats of fish and shellfish as dembu, such processed meats as sausages, frankfurters, and lever pastes, such leguminous products soybean curd, burnt soybean curd, fried soybean curd, deep-fried soybean curd, fried soybean curd cake with stuffed ingredients, frozen soybean curd, and yuba, such processed vegetables as puree, processed potatoes such as mashed potato, arrowroot starch, rice flour dumplings, boiled rice, rice vermicelli, macaroni, spaghetti, fine noodles, buckwheat noodles, noodles, chinese noodles, bread, biscuits, and sweetened bread cakes, such sweeteners as jam, such oils and fats as butter, margarine, mayonnaise, and dressing, such confectioneries as candy, rakugan, rice biscuits, sponge cake, adzuki-bean paste, bean-jam wafers, buns filled with bean jam, soft round rice cake stuffed with sweet bean jam, dumplings, uiro, chocolate, biscuits, cookies, doughnuts, cakes, pies, ice cream, budding, and Bavarian cream, such gel-like foodstuffs as soybean curd, jelly, konjak, agar, perilla, and gelidium jelly, and such seaweeds as kelp, wakame, laver, and agar weed may be cited.

The incorporation of the adsorbent in a processed food such as, for example, jelly may be accomplished by a procedure which comprises forming an unseasoned part (layer) and a seasoned part (layer) and incorporating the adsorbent in the unseasoned part (layer) or a procedure which comprises incorporating into the unseasoned jelly the adsorbent which has been seasoned in advance as described above with a view to preventing the adsorbent from adsorbing the seasoned part of the processed food.

Now, this invention will be described more specifically below with reference to working examples. It should be noted, however, that this invention is not limited to these working examples.

EXAMPLE 1

Production of Adsorbent (frozen active carbon-containing konjak)

In 750 ml of warm water kept at 30° C., a thorough mixture of 16 g of refined konjak flour and 4 g of active carbon having an average particle diameter of 15 $\mu$m was gently added piecemeal to the warm water lest it should form small wet lumps and then stirred and heated with strong fire for about five minutes. After the heated mixture began to boil, it was continuouly stirred over medium fire for 7–8 minutes and thereafter cooled to about 40° C. A solution of 0.64 g of CaO thoroughly ground in a mortar in 50 ml of warm water kept at 40° C. was added to the cooled mixture. They were quickly kneaded together. The resultant blend was placed in a pattern box and pressed thoroughly therein with finger tips to extract the entrapped air and homogenize the texture. The blend as held in the pattern box was placed in a bath of hot water, heated therein for about five minutes, removed from the pattern box, and further heated in hot water for 25 minutes until thorough coagulation to obtain 640 g of active carbon-containing konjak.

The portion, 500 g, of the active carbon-containing konjak produced as described above was placed in 1 liter of cold water, frozen therein at −30° C., left standing therein for five hours, then removed from the cold water, and thawed in hot water at 80° C. for one minute. The konjak was deprived of harshness by being left standing in a stream of water and cut into small dice, about 1 mm$^3$ in volume, to obtain the adsorbent of this invention (frozen active carbon-containing konjak).

EXAMPLE 2

Production of Adsorbent (frozen and dried active carbon-containing konjak)

An adsorbent of this invention (frozen and dried active carbon-containing konjak) was obtained by thoroughly drying 200 g of the adsorbent produced in Example 1 in a drier.

EXAMPLE 3

Production of Adsorbent (glycerin-added active carbon-containing konjak)

In 750 ml of an aqueous 5 wt. % glycerin solution kept at 30° C., a thorough mixture of 16 g of refined konjak flour and 16 g of active carbon having an average particle diameter of 30 μm was gently added piecemeal to the warm aqueous solution lest it should form small wet lumps and then stirred and heated with strong fire for about five minutes. After the heated mixture began to boil, it was continuouly stirred over medium fire for 7–8 minutes and thereafter cooled to about 40° C. A solution of 0.64 g of CaO thoroughly ground in a mortar in 50 ml of warm water kept at 40° C. was added to the cooled mixture. They were quickly kneaded together. The resultant blend was placed in a pattern box and pressed thoroughly therein with finger tips to extract the entrapped air and homogenize the texture. The blend as held in the pattern box was placed in a bath of hot water, heated therein for about five minutes, removed from the pattern box, and further heated in 1000 ml of an aqueous 5 wt. % glycerin solution for 25 minutes until thorough coagulation to obtain 650 g of glycerin-added active carbon-containing konjak. It was deprived of glycerin and freed from harshness by being left standing in a stream of water and cut into small dice, about 1 $mm^3$ in volume, to obtain the adsorbent of this invention (glycerin-added active carbon-containing konjak).

EXAMPLE 4

Production of Adsorbent (glycerin-added frozen active carbon-containing konjac)

The amount, 500 g, of the glycerin-added active carbon-containing konjok produced by following the procedure of Example 3 was frozen in liquefied nitrogen (–196° C.) and then thawed in warm water kept at 40° C. The konjak was deprived of glycerin and freed from harshness by being exposed to a stream of water and cut into dice, about 1 $mm^3$ in volume, to obtain an adsorbent of this invention (glycerin-added, frozen, active carbon-containing konjak).

EXAMPLE 5

Production of Adsorbent (glycerin-added, dried, and active carbon-containing konjak)

An adsorbent of this invention (glycerin-added, dried, and active carbon-containing konjak) was obtained by further drying thoroughly 200 g of the adsorbent produced in Example 3 in a drier.

EXAMPLE 6

Production of Adsorbent (glycerin-added, frozen, dried, and active carbon-containing konjak)

An adsorbent of this invention (glycerin-added, frozen, dried, and active carbon=-containing konjak) was obtained by further drying thorough 200 g of the adsorbent produced in Example 4 in a drier.

Control 1

Production of Adsorbent (active carbon-containing konjak)

An adsorbent for comparison (active carbon-containing konjak) was obtained by following the procedure of Example 1 while omitting the freezing and thawing treatments.

Control 2

Production of Adsorbent (dried active carbon-containing konjak)

An adsorbent for comparison (dried active carbon-containing konjak) was obtained by thoroughly drying 200 g of the adsorbent obtained in Control 1 in a drier.

EXAMPLE 7

Production of Adsorbent (frozen active carbon-containing calcium alginate gel ball)

A thorough mixture of 2 g of sodium alginate and 3 g of active carbon having an average particle diameter of 15 μm was added piecemeal as kept stirred into 800 ml of cold water. The resultant mixture was diluted with added water to a total volume of 100 ml and stirred for 24 hours to prepare a solution of sodium alginate containing 0.3 wt. % of active carbon. Separately, 11.1 g of calcium chloride was dissolved in 800 ml of distilled water and the resultant solution was diluted with added distilled water to a total amount of 1000 ml to prepare an aqueous 1.11 wt. % calcium chloride solution.

Then, the sodium alginate solution was introduced into a buret, 500 ml in volume, and added drop by drop into 500 ml of the calcium chloride solution mentioned above to obtain 10 g of crude gel balls of active carbon-containing calcium alginate. These crude gel balls were placed in a container, 5 liters in volume, and treated with a stream of deionized water for 10 hours to remove the unaltered reactants and the by-products and obtain gel balls of active carbon-containing calcium alginate.

Ten (10) g of the gel balls of active carbon-containing calcium alginate produced above were frozen at –85° C. and then thawed in hot water at 40° C. The gel balls were deprived of the unaltered reactants and the by-products by being exposed to a stream of water to produce an adsorbent of this invention (frozen gel balls of active carbon-containing calcium alginate).

EXAMPLE 8

Production of Adsorbent (gel balls of frozen, dried, and active carbon-containing calcium alginate)

An adsorbent of this invention (gel balls of frozen, dried, and active carbon-containing calcium alginate) was obtained by further drying thoroughly 10 g of the adsorbent produced in Example 7 in a drier.

EXAMPLE 9

Production of Adsorbent (gel balls of glycerin-added active carbon-containing calcium alginate)

A thorough mixture of 2 g of sodium alginate and 3 g of active carbon having an average particle diameter of 15 μm was added piecemeal as kept stirred into 800 ml of an aqueous 5 wt. % glycerin solution. The resultant mixture was diluted with added water to a total amount of 1000 ml and stirred for 24 hours to prepare a glycerin solution of sodium alginate containing 0.3 wt. % of active carbon. Separately, a solution of 11.1 g of calcium chloride in 800 ml of distilled water was diluted with added distilled water to a total amount of 1000 ml to obtain an aqueous 1.11 wt. % calcium chloride solution.

Then, the glycerin solution of sodium alginate mentioned above was poured into a buret, 50 ml in volume, and added drop by drop into 500 ml of the calcium chloride solution mentioned above to obtain 10 g of crude gel balls of glycerin-added active carbon-containing calcium alginate. The gel balls were placed in a container, 5 liters in volume, and deprived of the unaltered reactants and the by-products by being exposed to a stream of deionized water to obtain an adsorbent of this invention (gel balls of glycerin-added active carbon-containing calcium alginate).

EXAMPLE 10

Production of Adsorbent (gal balls of glycerin-added, frozen, and active carbon-containing calcium alginate)

The amount, 10 g, of the adsorbent produced in Example 9 was frozen at −85° C. and then thawed in hot water kept at 40° C. The adsorbent was deprived of the unaltered reactants and the by-products by being exposed to a stream of water to obtain an adsorbent of this invention (gel balls of glycerin-added, frozen, and active carbon-containing calcium alginate).

EXAMPLE 11

Production of Adsorbent (gel balls of glycerin-added, dried, and active carbon-containing calcium alginate)

An adsorbent of this invention (gel balls of glycerin-added, dried, and active-carbon-containing calcium alginate) was obtained by thoroughly drying 10 g of the adsorbent produced in Example 9 in a drier.

EXAMPLE 12

Production of Adsorbent (gel balls of glycerin-added, frozen, and active carbon-containing calcium alginate)

An adsorbent of this invention) gel balls of glycerin-added, frozen, dried, and active carbon-containing calcium alginate) was obtained by thoroughly drying 10 g of the adsorbent produced in Example 10 in a drier.

Control 3

Production of Adsorbent (gel balls of active carbon-containing calcium alginate)

An adsorbent for comparison (gel balls of active carbon-containing calcium alginate) was obtained by following the procedure of Example 7 while omitting the freezing and thawing treatments.

Control 4

Production of Adsorbent (gel balls of dried active carbon-containing calcium alginate)

An adsorbent for comparison (gel balls of dried and active carbon-containing calcium alginate) was obtained by thoroughly drying 10 g of the adsorbent produced in Control 3 in a drier.

EXAMPLE 13

Test for Evaluation of Speed of Adsorption

The adsorbents produced in Examples 1–12 and Controls 1–4 were tested for the ability to effect adsorption by measuring their speeds of adsorption.

In a 300-ml beaker, a 1-g sample weighed out of the relevant adsorbent was placed and made to add 50 ml of a dilute blue ink solution (0.112 in absorbance). The dilute ink solution, as kept stirred with the sample, was measured at intervals along the course of time for the absorbance at a wavelength of 475 nm to find as the speed of adsorption the duration between the time the ink solution was added and the time the absorbance fell below 0.01. The results are shown in Table 1. The conditions under which the adsorbents were treated are additionally shown in the table.

TABLE 1

| Absorbent | Gel-like substance | Freezing treatment (Yes/No) | Drying treatment (Yes/No) | Addition of glycerin (Yes/No) | Speed of adsorption (in minute) |
|---|---|---|---|---|---|
| Example 1 | Konjak | Yes | No | No | 7 |
| Example 2 | Konjak | Yes | Yes | No | 15 |
| Example 3 | Konjak | No | No | Yes | 1 |
| Example 4 | Konjak | Yes | No | Yes | 3 |
| Example 5 | Konjak | No | Yes | Yes | 10 |
| Example 6 | Konjak | Yes | Yes | Yes | 5 |
| Example 7 | Calcium alginate gel | Yes | No | No | 15 |
| Example 8 | Calcium alginate gel | Yes | Yes | No | 20 |
| Example 9 | Calcium alginate gel | No | No | Yes | 10 |
| Example 10 | Calcium alginate gel | Yes | No | Yes | 15 |
| Example 11 | Calcium alginate gel | No | Yes | Yes | 15 |
| Example 12 | Calcium alginate gel | Yes | Yes | Yes | 20 |
| Control 1 | Konjak | No | No | No | 200 |
| Control 2 | Konjak | No | Yes | No | 150 |
| Control 3 | Calcium alginate gel | No | No | No | 70 |
| Control 4 | Calcium alginate gel | No | Yes | No | 140 |
| Simple substance of active carbon | No | No | No | No | 5 |

EXAMPLE 14

Test for Removal of Coloring Material [food dye red No. 104 (Floxin)] by Adsorption The coloring materials allowed for addition to food are used for the purpose of beautifying the food or imitating the tint of natural color of the food. In the synthetic tar type dyes, only such water-soluble dyes as the food dye red No. 104 are allowed at present for use in food. Their use is restricted.

The adsorbents produced in Example 3 and Control 1 were tested for removal by adsorption of the food dye red No. 104 used in sausage. Twenty (20) g of sausage was finely ground. The ground sausage and 0.5 g of a given adsorbent and 100 ml of water added thereto were kept stirred. Liquid layers collected meanwhile in a fixed volume of 10 ml at intervals of a fixed length along the course of time were each dissolved in five times its volume of hot water and then centrifuged. The supernatant consequently obtained were used as test solutions. The test solutions were treated by the method described at pages 146–149 of the "Pictorial Guide to Method for Testing Food Hygiene" compiled by Misao Haruta et al. and published by Chuo Hoki Press, with necessary modifications, and rated for efficiency of removal by the filter paper chromatography.

The time which elapsed until the detection of the food dye red No. 104 ceased to exist was one minute in the case of the adsorbent of Example 3, whereas it was 10 minutes in the case of the adsorbent of Control 1.

EXAMPLE 15
Test for Removal of Preservative [orthophenyl phenol (OPP)] by Adsorption Orthophenyl phenol shows clear signs of carcinogenicity and teratogenesis similarly to Thiambendazol (TBZ). This preservative is effective in inhibiting the growth of fungi and various species of aerobic and anaerobic bacteria and used in a wide variety of processed foodstuffs.

The adsorbents produced in Example 10 and Control 3 were tested for removal by adsorption of orthophenyl phenol in orange. In a beaker, 50 g of a sample obtained by finely cutting orange was placed. The sample and about 100 ml of water and one g of a given adsorbent added thereto were kept stirred.

Liquid layers collected meanwhile in a fixed volume of 10 ml at intervals of a fixed length along the course of time were used as test solutions. The test solutions were treated by the method described at pages 142–143 of the "Pictorial Guide to Method for Testing Food Hygiene" compiled by Misao Haruta et al. and published by Chuo Hoki Press, with necessary modifications, and tested for orthophenyl phenol concentration.

The time which elapsed until the orthophenyl phenol concentration fell below the limit of detection (0.01 ppm) was three minutes in the case of the adsorbent of Example 10, whereas it was 10 minutes in the case of the adsorbent of Control 3.

EXAMPLE 16
Test for Removal of Antioxidant [dibutyl hydroxy toluene (BHT)] by Adsorption The antioxidant is effective in preventing loss of texture, keeping the nutritive value of food from being degraded by oxidation, preventing the processed fishery product from being sunburned, and preventing a dye from being browned besides protecting oils and fats against putrefaction by acid. It is used in a rich variety of foodstuffs.

The adsorbents produced in Example 10 and Control 3 were tested for removal of dibutyl hydroxy toluene by adsorption in chewing gum. In a 500-ml eggplant-shaped flask connected to a continuous extractor fitted with a reflux condenser, 5 g of chewing gum, 50 g of NaCl, 0.2 g of pyrogallol, 200 ml of water, boiling tips, and 1 g of a given adsorbent were subjected to continuous extraction. Meanwhile, 10-ml extracted solutions were collected at intervals of a fixed length and used as test solutions. The test solutions were treated by the method described at pages 158–159 of the "Pictorial Guide to Method for Testing Food Hygiene" compiled by Misao Haruta et al. and published by Chuo Hoki Press, with necessary modifications, and tested by the gas chromatography for dibutyl hydroxy toluene.

The time which elapsed until the dibutyl hydroxy toluene concentration fell below the limit of detection (0.01 g/kg) was four minutes in the case of the adsorbent of Example 10, whereas it was 10 minutes in the case of the adsorbent of Control 3.

EXAMPLE 17
Test for Removal of Fungicide (hydrogen peroxide) by Adsorption

Hydrogen peroxide possesses a powerful oxidizing action and a fungicidal power. The use of this fungicide has been banned since the oral ingestion thereof to mice was recognized to induce a cancer growth, though feebly, in the duodenum. At present, it is used only on herring roe.

The adsorbents produced in Example 3 and Control 1 were adopted and tested for removal by adsorption of hydrogen peroxide in herring roe. About 5 g of finely cut herring roe was placed in an attriting cup and then stirred vigorously for 3 minutes with 40 ml of an exuding solution added thereto, with the cup ice cooled externally. The resultant mixture and 0.3 g of a given adsorbent added thereto were kept stirred. Liquid layers were collected meanwhile in a fixed volume of 10 ml at intervals of a fixed length along the course of time. They were deprived of bubbles formed therein by the addition of 0.1 ml of silicone, diluted with added water to a total amount of 50 ml, and then thoroughly stirred and filtered. The filtrates, with the first 5-ml fractions thereof discarded, were used without any modification as test solutions. These test solutions were treated by the method described at pages 144–145 of the "Pictorial Guide to Method for Testing Food Hygiene" compiled by Misao Haruta et al. and published by Chuo Hoki Press, with necessary modifications, and tested for hydrogen peroxide concentration by the measurement of oxygen potential.

The time which elapsed until the hydrogen peroxide concentration fell below the limit of detection (0.01 ppm) was one minute in the case of the adsorbent of Example 3, whereas it was five minutes in the case of the adsorbent of Control 1.

EXAMPLE 18
Test for Removal of Bleaching Agent (sulfurous acid) by Adsorption Sulfurous acid and salts thereof are effective not only in bleaching food but also in preserving food and preventing food from oxidation and, therefore, are used as additives for numerous foodstuffs. Depending on the sort of foodstuff, their use is restricted with the amount of residual sulfur dioxide as a criterion.

The adsorbents produced in Example 1 and Control 1 were adopted and tested for removal by adsorption of sulfuric acid in dried gourd shavings. The amount, 0.2 g, of finely sliced dried gourd shavings were kept stirred with 0.2 g of a given adsorbent and 20 ml of distilled water added thereto. Liquid layers collected meanwhile in a fixed volume of 10 ml at intervals of a fixed length along the course of time were used as test solutions. These test solutions were treated by the method described at pages 150–151 of the "Pictorial Guide to Method for Testing Food Hygiene" compiled by Misao Haruta et al. and published by Chuo Hoki Press, with necessary modifications, and tested for sulfurous acid concentration by the modified Rankine method.

The time which elapsed until the sulfurous acid concentration fell below the limit of detection (160 ppm) was five minutes in the case of the adsorbent of Example 1, whereas it was ten minutes in the case of the adsorbent of Control 1.

EXAMPLE 19
Test for Removal of Female Hormone (Estradiol) by Adsorption

The adsorbents produced in Example 3 and Control 1 were adopted and tested for removal by adsorption of Estradiol in beef. A 25-g sample taken from the meat of a bull which had consumed a feed incorporating Estradiol therein was increased to a total weight of 50 g by adding water. The sample plus the water and 7 g of a given adsorbent were kept stirred. Liquid layers were collected meanwhile in a fixed volume of 10 ml at intervals of a fixed length along the course of time and centrifuged at 5000 rpm. The supernatant consequently formed were adopted as test solutions. These test solutions were tested for Estradiol concentration in accordance with the method of radioimmunoassay (RIA) [page 818 in the 30th revised edition of the "Glossary of Clinical Test Methods" compiled by Masamitsu Kanai and published by Kanahara Publishing K.K.] using an Estradiol testing kit (Estradiol=antibody kit made by Nippon DPC K.K.).

The time which elapsed until the Estradiol concentration fell below the limit of detection (5 pg/ml) was 1.5 minutes in the case of the adsorbent of Example 3, whereas it was ten minutes in the case of the adsorbent of Control 1.

EXAMPLE 20
Test for Removal by Adsorption of Female Hormone (Estradiol) in Milk The adsorbents produced in Example 3 and Control 1 were adopted and tested for removal by adsorption of Estradiol in milk. A stainless steel column measuring 3 mm in thickness, 6 cm in inside diameter, and 100 cm in length was packed with lumps of a given adsorbent (5 mm×3 mm×1.5 mm) to manufacture a column for removal by adsorption. Into this column, 5 liters of raw milk (fat ratio 3.0%) containing 300 pg/ml of Estradiol was introduced at a flow speed of 2.8 liters/minute. The treated milk eluted from the column was collected in a fixed fraction of 30 g at intervals of a fixed length along the course of time. These fractions and 150 g of $H_2O$ added thereto were stirred for 30 minutes and centrifuged at 10000 rpm. The supernatant obtained consequently were used as samples. These samples were tested for Estradiol concentration in the same manner as in Example 19. The time which elapsed until the Estradiol concentration fell below the limit of detection (5 pg/ml) was three minutes in the case of the adsorbent of Example 3, whereas it was 30 minutes in the case of the adsorbent of Control 1.

EXAMPLE 21
Test for Removal by Adsorption of Organic Phosphur Agent (Diazinone)

To date, 35 kinds of organic phosphorus agents have been registered as insecticides, 3 kinds thereof as fungicides, and 8 kinds thereof as herbicides. On account of low residue and low toxicity, they have found extensive utility.

The adsorbents produced in Example 9 and Control 3 were adopted and tested for removal by adsorption of Diazinone in apples. A 20-g sample of slices of apple was placed in 100 ml of acetone and intimately mixed by the use of a high-speed homogenizer for five minutes. The resultant mixture and 1 g of a given adsorbent added thereto were kept stirred. Liquid layers were collected meanwhile in a fixed volume of 10 ml at intervals of a fixed length along the course of time, filtered with a funnel made by Kiriyama K.K. (filter aid 5 mm), and further subjected to extraction filtration with 100 ml of 30% hydrated acetone. The filtrates consequently obtained were used as test solutions. These test solutions were treated by the method described at pages 94–95 of the "Pictorial Guide to Method for Testing Food Hygiene" compiled by Misao Haruta et al. and published by Chuo Hoki Press, with necessary modifications, and tested by the gas chromatography for Diazinone concentration.

The time which elapsed until the Diazinone concentration fell below the limit of detection (10 ppb) was three minutes in the case of the adsorbent of Example 9, whereas it was five minutes in the case of the adsorbent of Control 3.

EXAMPLE 22
Test for Removal by Adsorption of Organic Chlorine Agent [Chlorosalonyl (TPN)]

Since organic chlorine agents pose the problems of toxicity and residue, their use has been banned to date nearly completely. Only Chlorosalonyl (TPN), PCNB, phthalimide type agents, Chlorobenzylates, etc. are still used today as fungicides and miticides.

The adsorbents produced in Example 10 and Control 3 were adopted and tested for removal by adsorption of Chlorosalonyl in cucumbers. A 20-g sample of slices of cucumber was placed in 100 ml of acetone and intimately mixed by the use of a high-speed homogenizer for five minutes. The resultant mixture and 1 g of a given adsorbent added thereto were kept stirred. Liquid layers were collected meanwhile in a fixed volume of 10 ml at intervals of a fixed length along the course of time and subjected to extraction. The extracts consequently obtained were used as test solutions. These test solutions were treated by the method described at pages 94–95 of the "Pictorial Guide to Method for Testing Food Hygiene" compiled by Misao Haruta et al. and published by Chuo Hoki Press, with necessary modifications, and tested by the gas chromatography for Chlorosalonyl concentration.

The time which elapsed until the Chlorosalonyl concentration fell below the limit of detection (0.001 ppm) was three minutes in the case of the adsorbent of Example 10, whereas it was ten minutes in the case of the adsorbent of Control 3.

EXAMPLE 23
Test for Removal by Adsorption of Carbamate Agent

To date, 11 kinds of carbamate agents have been registered as insecticides and 8 kinds thereof as herbicides. On account of low toxicity and low residue, they find extensive utility as insecticides similarly to the organic phosphorus agents.

The adsorbents produced in Example 3 and Control 1 were adopted and tested for removal by adsorption of a carbamate agent in tomatoes. A 20-g sample of slices of tomato was placed in 100 ml of acetone and intimately mixed by the use of a high-speed homogenizer for five minutes. The resultant mixture and 1 g of a given adsorbent added thereto were kept stirred. Liquid layers were collected meanwhile in a fixed volume of 10 ml at intervals of a fixed length along the course of time and subjected to extraction. The extracts consequently obtained were used as test solutions. These test solutions were treated by the method described at pages 102–103 of the "Pictorial Guide to Method for Testing Food Hygiene" compiled by Misao Haruta et al. and published by Chuo Hoki Press, with necessary modifications, and tested by the gas chromatography for carbamate agent concentration.

The time which elapsed until the carbamate agent concentration fell below the limit of detection (0.001 ppm) was one minute in the case of the adsorbent of Example 3, whereas it was ten minutes in the case of the adsorbent of Control 1.

EXAMPLE 24
Test for Removal by Adsorption of Autotoxin (Solanine)

Solanine is an alkaloid glycoside which is present in the parts of new buds of potato. The $LD_{50}$ of this compound, when orally ingested to a rabbit, is 0.45 g/kg. In human beings, it causes poisoning at a concentration of 0.2–0.4 g.

The adsorbents produced in Example 9 and Control 3 were adopted and tested for removal by adsorption of solanine in potato. A 5-g sample of slices of potato was placed in 30 ml of methanol and intimately mixed by the use of a homogenizer for five minutes. The resultant mixture and 0.5 g of a given adsorbent added thereto were kept stirred. Liquid layers were collected meanwhile in a fixed volume of 10 ml at intervals of a fixed length along the course of time and subjected to extraction. The extracts consequently obtained were used as test solutions. These test solutions were treated by the method described at pages 82–83 of the "Pictorial Guide to Method for Testing Food Hygiene" compiled by Misao Haruta et al. and published by Chuo Hoki Press, with necessary modifications, and tested by the liquid chromatography for solanine concentration.

The time which elapsed until the solanine concentration fell below the limit of detection (0.001 ppm) was one minute in the case of the adsorbent of Example 9, whereas it was five minutes in the case of the adsorbent of Control 3.

EXAMPLE 25

Test for Removal by Adsorption of Histamine

Such fishes of red flesh as mackerel, horse mackerel, and saury which tend to cause such food poisoning as allergy have high free histidine contents in their muscles. When these fishes are contaminated with bacteria of strong histidine decarboxylase activity and weak histaminase activity, they suffer accumulation of histamine.

The adsorbents produced in Example 1 and Control 1 were adopted and tested for removal by adsorption of histamine in mackerel. A 10-g sample of muscles of mackerel was placed in 15 ml of water and homogenizer for five minutes. The resultant mixture and one g of a given adsorbent added thereto were kept stirred. Liquid layers were collected meanwhile in a fixed volume of 10 ml at intervals of a fixed length along the course of time and adopted as test solutions. These test solutions were treated by the method described at pages 134–135 of the "Pictorial Guide to Method for Testing Food Hygiene" compiled by Misao Haruta et al. and published by Chuo Hoki Press, with necessary modifications, and tested by the liquid chromatography for histamine concentration.

The time which elapsed until the histamine concentration fell below the limit of detection (2.5 mg/100 g) was seven minutes in the case of the adsorbent of Example 1, whereas it was ten minutes in the case of the adsorbent of Control 1.

EXAMPLE 26

Test for Removal by Adsorption of Cadmium

Cadmium is widely distributed in the natural world and used in large quantities on a commercial scale. The pollution of the environment by the cadmium so used copiously in the industry and the contamination of human organisms by the cadmium through the medium of foodstuffs have become a subject of discussion. Cadmium, when orally ingested in a large amount, induces an acute gastrointestinal trouble and, when ingested in a minute amount, induces a renal trouble. The daily intake of cadmium by the Japanese roughly averages 30–60 $\mu$g. It is estimated that 30–40% of the average originates in rice.

The adsorbents produced in Example 4 and Control 1 were adopted and tested for removal by adsorption of cadmium in unpolished rice. In a reaction vessel, 10 g of finely ground unpolished rice, 3 g of a given adsorbent, 40 ml of distilled water, and sulfuric acid were placed sequentially in the order mentioned and were gradually heated together. When the liquid product of decomposition assumed a light yellow clear texture, it was cooled and diluted with distilled water to a total volume of 100 ml. The dilute liquid was adopted as a test solution. This test solution was treated by the method described at pages 126–127 of the "Pictorial Guide to Method for Testing Food Hygiene" compiled by Misao Haruta et al. and published by Chuo Hoki Press, with necessary modifications, and tested by the atomic adsorptiometric method for cadmium concentration.

The time which elapsed until the cadmium concentration fell below the limit of detection (0.02 ppm) was three minutes in the case of the adsorbent of Example 4, whereas it was ten minutes in the case of the adsorbent of Control 1.

EXAMPLE 27

Test for Removal by Adsorption of Diethylene Glycol (DEG)

Diethylene glycol (DEG) is used as a solvent for the automobile antifreezing solution, brake oil compound, cellophane softener, and rubber oil and fat. The toxicity $LD_{50}$ of this compound, when orally ingested into human beings, is held to be 1000 mg/kg. The fact that the diethylene glycol the use of which as a food additive was banned in 1985 has been incorporated in foreign wines for the purpose of adding to the body and sweetness of fine and these foreign wines have been imported to our country has been divulged and has become a subject of discussion.

The adsorbents produced in Example 4 and Control 1 were adopted and tested for removal by adsorption of diethylene glycol. Diethylene glycol was dissolved in methanol at a concentration of 100 $\mu$g/ml to prepare the solution in an amount of 100 g. Forty (40) g of this solution and 3 g of a given adsorbent were kept stirred. Liquid layers were collected meanwhile in a fixed volume of 10 ml at intervals of a fixed length along the course of time and subjected to extraction. The extracts were concentrated at 45° C. and then diluted with added water to 10 ml and the produced dilute solutions were adopted as test solutions. These solutions were treated by the method described at pages 114–115 of the "Pictorial Guide to Method for Testing Food Hygiene" compiled by Misao Haruta et al. and published by Chuo Hoki Press, with necessary modifications, and tested by the gas chromatography method for diethylene glycol concentration.

The time which elapsed until the diethylene glycol concentration fell below the limit of detection (10 ppm) was three minutes in the case of the adsorbent of Example 4, whereas it was ten minutes in the case of the adsorbent of Control 1.

EXAMPLE 28

Test for Prevention of Hangover (removal by adsorption of acetaldehyde)

The adsorbents produced in Example 3 and Control 1 were adopted and tested for prevention of hangover. Of a panel of 20 adult male members, 10 members each ingested 10 g of the adsorbent of Example 3 and 10 members each ingested 10 g of the adsorbent of Control 1 immediately before they began drinking an average of 500 ml of alcohol beverage (Japanese sake having an alcohol content of 16%) per head over a period of two hours.

When the physical conditions of the panel members were visually examined individually after 12 hours of drinking the alcohol beverage, none of the ten members of the group which took the adsorbent of Example 3 before the drinking either felt nausea or felt sick, whereas six of the 10 members of the group which took the adsorbent of Control 1 before the drinking felt sick and none of them felt nausea or ill.

EXAMPLE 29

Test for Prevention of Degradation of Oil (removal by adsorption of hydroperoxide)

The adsorbents produced in Example 6 and Control 1 were adopted and tested for prevention of degradation of oil. Five hundred (500) ml of sesame oil was heated to 145–150° C. and deeply fried 50 g of carp for ten minutes. The oil was cooled to 28±1° C. and then heated again to 145–150° C. The deep frying of carp with the same oil was performed up to ten repetitions. Ten (10) g of a given adsorbent was placed in a covered stainless steel basket, placed in the used oil, and rated for offensive odor, color, foaming property, viscosity, separation of oil, and smoke (230–240° C.) in comparison with the adsorbent in an unused oil to determine the degree of degradation of the oil.

The time which elapsed until the assumption of the degradation by the used oil completely ceased to exist as compared with the unused oil was ten minutes in the case of the adsorbent of Example 6, whereas it was 30 minutes in the case of the adsorbent of Control 1.

EXAMPLE 30

Test for Deodorization of Old Rice (removal by adsorption of carbonyl compound)

It is said that when old rice is boiled and stored at a high temperature in high humidity, it induces decomposition of fatty acids, forms such carbonyl compounds as n-valeoaldehyde and n-caproaldehyde, and assumes the odor peculiar to old rice.

The adsorbents produced in Example 3 and Control 2 were each molded in the form of spheres (about 2 cm in diameter) and tested for deodorization of old rice. Boiled rice was obtained by washing 540 g of the old rice with water, placing the washed rice in an automatic rice cooker, immersing a given adsorbent in the washed rice, dipping the rice in water of an adjusted amount, and boiling the rice.

The number of adsorbent spheres required for thorough removal of the odor of old rice was one in the case of the adsorbent of Example 3, whereas it was three in the case of the adsorbent of Control 1.

EXAMPLE 31

Test for Removal by Adsorption of *E. coli* BEROTOKISHIN

The adsorbent produced in Example 4 was adopted and tested for removal by adsorption of the toxin (BEROTOKISHIN types 1 and 2) produced by the strain 0157 of the pathogenic *E. coli*. The reagent, culture medium, and *E. coli* used in the test were as follows.

Reagent:

*E. coli* BEROTOKISHIN detection kit (made by Denka Seiken K.K.)
CA-YE culture medium:

| | |
|---|---|
| Casamino acid | 20 g |
| Yeast extract | 6 g |
| NaCl | 2.5 g |
| $K_2HPO_4$ | 8.71 g |
| Salt solution* | 1 ml |
| Distilled water | 1000 ml | pH 8.5 (1N NaOH used)
Composition of salt solution

| | |
|---|---|
| $MgSO_4$ | 5% |
| $MnCl_2$ | 0.5% |
| $FeCl_3$ | 0.5% |

The reagent was dissolved in 0.001N $H_2SO_4$.
LB culture medium

| | |
|---|---|
| Bactotrypton | 10 g |
| Yeast extract | 5 g |
| NaCl | 5 g |
| Distilled water | 1000 ml | pH 7.2 (1N NaOH used)

*E. coli*

TT-11 (microbe offered by National Infant Medical Center)

In sterilized test tubes, the CA-YE culture medium was dispensed in a fixed volume of 10 ml and the microbe was inoculated to the culture medium by the use of a platinum wire and the culture medium was vigorously shaken (120 cycles/min.) for culture at 37° C. for 18 hours. The culture broth was centrifuged at 4° C. at 3500 rpm for 20 minutes and subjected to filtration sterilization by the use of 0.45 $\mu$m of Acrodisc. The filtrate was dispensed in tubes in a fixed volume of 2 ml and then mixed for ten minutes with a given adsorbent added thereto in a prescribed amount and subsequently left standing at rest at 4° C. for 24 hours. The mixed solutions were centrifuged at 4° C. at 3000 rpm for 20 minutes and then filtered with 0.45 $\mu$m of Acrodics. The filtrates consequently obtained were adopted as test solutions.

To each of the test solutions, a diluent was added dropwise in a fixed volume of 25 $\mu$l in a total of eight wells in three rows of a microplate (U type) with the aid of a dropper. For the control of BEROTOKISHIN, the diluent was added dropwise in a fixed volume of 25 $\mu$l in a total of eight wells two rows with the aid of a dropper. The test solutions excepting those in the final well (the final well using latex as control) were diluted to two degrees. Similarly, the control BEROTOKISHIN Type 1 and type 2 were respectively diluted in two degrees per row. A sensitized latex VT1 was added dropwise to the first row of the diluted series of test solution, a sensitized latex VT12 to the second row thereof, and a control latex to the third row thereof respectively in a fixed volume of 25 $\mu$l. The sensitized latex VT1 was added dropwise to the diluted series of the control BEROTOKISHIN type 1 and sensitized latex VT2 to the diluted series of the control BEROTOKISHIN type 2 respectively in a fixed volume of 25 $\mu$l. The microplate was thoroughly shaken to ensure intimate mixture of the test solutions and the latex reagents. The microplate was covered to preclude vaporization of the reaction solutions, left standing at rest at room temperature for not less than 20 hours, and then mounted on a black sheet of paper spread on a bright flat place. The images of latex sediments in the individual wells of the plate were observed with an unaided eye by way of evaluation of qualities. The results of the removal by adsorption of the BEROTOKISHIN type 1 and type 2 are shown respectively in Table 2 and Table 3.

TABLE 2

| Visual observation of images of latex precipitates in wells | | | | | | | | |
|---|---|---|---|---|---|---|---|---|
| (VT1) (CA-YE culture medium) | 1 | 2 | 4 | 8 | 16 | 32 | 64 | 128 | Control |
| Absorbent (0.2 g) | | – | – | – | – | – | – | – | – |
| Absorbent (0.1 g) | | – | – | – | – | – | – | – | – |
| TT-11 (Control) | | + | + | + | + | + | ± | – | – |

TABLE 3

Visual observation of images of latex precipitates in wells

| | 1 2 | 4 | 8 | 16 | 32 | 64 | 128 | 256 | 512 | Control |
|---|---|---|---|---|---|---|---|---|---|---|
| (VT1) (CA-YE culture medium) | | | | | | | | | | |
| Absorbent (0.2 g) | − − | − | − | − | − | − | − | − | − | − |
| Absorbent (0.1 g) | − − | − | − | − | − | − | − | − | − | |
| TT-11 (Control) | + + | + | + | + | + | + | + | ± | − | − |

EXAMPLE 32

Test for Preventing Diarrhea Caused by Oral Ingestion of Antibiotic Substance (Erythromycin)

To a group of six rabbits, 3.0–3.2 kg in body weight, Erythromycin was orally ingested 12 times at intervals of 6 hours in a fixed amount of 40 mg per head each time by the use of fixed feed. The adsorbent produced in Example 6 was orally ingested to the rabbits in a fixed amount of 3 g per head 30 minutes prior to each round of the ingestion.

The symptom of diarrhea was manifested in 100% of the rabbits of the group not using the adsorbent and 0% of the rabbits of the group using the adsorbent. At this time, in the group of rabbits taking the adsorbent and the group of rabbits not taking the adsorbent alike, the concentration of Erythromycin in the blood measured 1.5 hours after the oral ingestion was invariably in the range of 0.12–0.13 $\mu$g/ml.

EXAMPLE 33

Test for Prevention of Diarrhea Caused by Oral Ingestion of Antibiotic Substance (Erythromycin)

A male, 60 years in age and 78 kg in body weight, was made to eat meals at intervals of six hours and take orally 300 mg of Erythromycin 5 minutes after each meal. The symptom of diarrhea manifested itself on the 18th oral ingestion. Then, the oral ingestion was discontinued.

The same male was made to take ordinary meals for one month after the recovery from the diarrhea and then take orally Erythromycin in the same manner as above and also take orally 10 g of the adsorbent produced in Example 2 30 minutes prior to each of the meals. No symptom of diarrhea manifested itself even on the 20th oral ingestion.

EXAMPLE 34

Production of Adsorbent-containing Agar

In one liter of a boiling decoct of dried bonito, 100 g of the adsorbent produced in Example 1 was boiled for three minutes. A 10-g sample of the produced soup was placed in an aluminum container, 30 cm$^3$ in inner volume, and was thoroughly mixed with 15 g of an agar solution added thereto. The resultant mixture was deaerated, then hot sealed with a lid of aluminum foil, and sterilized in an autoclave at 121° C. for 20 minutes to obtain an adsorbent-containing agar.

EXAMPLE 35

Production of Adsorbent-containing Agar

An adsorbent-containing agar was obtained by following the procedure of Example 34 while using the adsorbent produced in Example 3 instead.

EXAMPLE 36

Production of Adsorbent-containing Agar

In an aluminum container, about 50 cm$^3$ in inner volume, 10 g of the adsorbent-containing agar produced by following the procedure of Example 34 was placed and 20 g of an agar solution was added thereto. On the resultant mixture, a kelp seasoned with salad oil of Chinese fashion was superposed and 10 g of the agar solution was further added thereon. The resultant mixture was deaerated and, with the container heat sealed with a lid of aluminum foil, sterilized in an autoclave at 121° C. for 20 minutes to obtain an adsorbent-containing agar.

EXAMPLE 37

Production of Adsorbent-containing Calcium Alginate Gel

An adsorbent-containing calcium alginate gel was obtained by following the procedure of Example 34 while using the adsorbent produced in Example 3 instead and using calcium alginate gel in the same amount instead of the agar solution.

EXAMPLE 38

Production of Adsorbent-containing Calcium Alginate Gel

An adsorbent-containing calcium alginate gel was obtained by following the procedure of Example 37 while using the adsorbent produced in Example 9 instead.

EXAMPLE 39

Production of Adsorbent-containing Calcium Alginate Gel

An adsorbent-containing calcium alginate gel was obtained by following the procedure of Example 36 while using the adsorbent produced in Example 4 instead and using calcium alginate gel in the place of the agar solution.

Industrial Applicability

The adsorbent of this invention is obtained by coating an adsorption basis with a gel-like substance and then subjecting the coated absorption basis to a freezing treatment and is formed of a dispersed system having the adsorption basis uniformly dispersed in the gel-like substance and, therefore, is capable of effecting removal by adsorption of a harmful substance with unusually high efficiency without sacrificing the adsorbing ability which is inherent in the adsorption basis.

The adsorbent of this invention can manifest the same effect as mentioned above because it is obtained by coating an adsorption basis with a gel-like substance already containing a frost harm preventing substance and subsequently depriving the coated adsorption basis of the front harm preventing substance.

Further, the adsorbent of this invention, when adopting minute particles of powdered active carbon, for example, as the adsorption basis, is allowed to form a dispersed system having the adsorption basis uniformly dispersed in a gel-like substance. It is, therefore, capable of effecting removal by adsorption of a harmful substance with unusually high efficiency because the adsorbent as a whole enjoys an increased area available for adsorption and a consequent increase in the ability to effect adsorption as compared with the active carbon which is used all by itself owing to the addition to the efficiency of dispersion of active carbon.

Since the adsorbent of this invention has an adsorption basis coated with a gel-like substance, it can be directly ingested into the digestive system and can easily effect removal by adsorption of the harmful substance introduced as mixed with a foodstuff into the digestive system. Moreover, this adsorbent avoids inducing such a trouble as constipation even when it is directly ingested into the digestive system. The adsorbent which has effected the removal by adsorption of the harmful substance in the digestive system can be very quickly and easily discharged from the digestive system.

The adsorbent of this invention can be made to effect the removal by adsorption of the harmful substance contained in a foodstuff by being brought into direct contact with the foodstuff. In this case, the adsorbent which has effected the removal by adsorption of the harmful substance can be separated easily and quickly from the foodstuff as compared with the adsorbent which is used all by itself. Even when the adsorbent erroneously mingles into a foodstuff and ultimately reaches the interior of the digestive system without being separated, it is safe all the same because it is quickly discharged from the digestive system as described above.

The adsorbent of this invention, besides being utilized for direct ingestion into the digestive system as described above, can be utilized as mixed with a processed foodstuff, for example. When the adsorbent of this invention is fixed with a processed foodstuff and the resultant mixture is eaten, it avoids imparting a sensation of the presence of foreign matter, excels in palatability, and precludes the possibility of tainting the foodstuff in black tint.

Since the adsorbent of this invention manifests the outstanding effect mentioned above, it is particularly useful for the removal by adsorption of such food additive, feed additive, agricultural pesticide, food poisoning substance, allergen, heavy metal or highly poisonous organic compound as are suffered to adhere to or exist in the foodstuffs, such surplus nutrients as persist in the digestive system, such oligomers and additives as are contained in liquors, such metabolites of alcohol as are formed in the digestive system after assimilation of alcohol, such harmful substances as hydroperoxides of unsaturated fatty acids as are suffered to exist in oils and fats, and such components of offensive odor as emanate from fish.

What is claimed is:

1. An adsorbent formed by coating an adsorption basis with a gel substance already containing a frost damage preventing substance and subsequently depriving the coated basis partly or wholly of said frost damage preventing substance wherein said frost damage preventing substance is glycerin.

2. An adsorbent according to of claim 1, wherein said adsorption basis is a carbonaceous material possessing the ability to effect adsorption.

3. An adsorbent according to claim 2, wherein said carbonaceous material possessing the ability to effect adsorption is active carbon or charcoal.

4. An adsorbent formed by drying an adsorbent set forth in claim 1.

5. An agent for removal by adsorption of a harmful substance, which comprises an adsorbent set forth claim 1.

6. An agent according to claim 5, wherein said harmful substance is a food additive, a feed additive, an agricultural pesticide, a food poisoning substance, allergen, a heavy metal, or a strongly poisonous organic compound which is suffered to adhere to or mingle in a foodstuff or an animal feed or assimilated into the digestive system.

7. An agent according to claim 6, wherein said feed additive is an antibiotic substance, a synthetic antibacterial agent, or a hormone agent.

8. An agent according to claim 6, wherein said food poisoning substance is exotoxins, autotoxins, or a harmful chemical substance.

9. An agent according to claim 5, wherein said harmful substance is formed of an antibiotic substance which has either undergone oral ingestion or acted on the intestinal bacteria.

10. An agent for the removal by adsorption of a surplus nutrient assimilated in the digestive system, which agent comprises an adsorbent set forth in claim 1.

11. An agent for the removal by adsorption of the intermediate metabolite of alcohol formed in the digestive system in consequence of the assimilation of said alcohol, which agent comprises an adsorbent set forth in claim 1.

12. An agent for the removal by adsorption of hydroperoxide of an unsaturated fatty acid in oil or fat, which agent comprises an adsorbent formed by coating an adsorption basis with a gel substance and subsequently subjecting the coated basis to a freezing treatment.

13. A deodorant comprising an adsorbent formed by coating an adsorption basis with a gel substance and subsequently subjecting the coated basis to a freezing treatment.

14. A process foodstuff or animal feed incorporating therein 0.01–60 wt. % of an adsorbent formed by coating an adsorption basis with a gel substance and subsequently subjecting the coated basis to a freezing treatment.

15. A processed foodstuff according to claim 14, which is a dairy product, a product of fish paste, a processed fish or shellfish, a processed meat, processed beans, processed vegetables, a processed potato, a processed cereal, a sweetener, oil and fat, or a cake.

16. An agent for the removal by adsorption of hydroperoxide of an unsaturated fatty acid in oil or fat, which agent comprises an adsorbent formed by coating an adsorption basis with a gel substance already containing a frost damage preventing substance and subsequently depriving the coated basis partly or wholly of said frost damage preventing substance wherein said frost damage preventing substance is glycerin.

17. A deodorant comprising an adsorbent formed by coating an adsorption basis with a gel substance already containing a frost damage preventing substance and subsequently depriving the coated basis partly or wholly of said frost damage preventing substance wherein said frost damage preventing substance is glycerin.

18. A process foodstuff or animal feed incorporating therein 0.01–60 wt. % of an adsorbent formed by coating an adsorption basis with a gel substance already containing a frost damage preventing substance and subsequently depriving the coated basis partly or wholly of said frost damage preventing substance.

* * * * *